United States Patent [19]
Hisada et al.

[11] Patent Number: 5,851,205
[45] Date of Patent: Dec. 22, 1998

[54] DISPOSABLE UNDERGARMENT HAVING A TAPE FASTENER

[75] Inventors: Kenichi Hisada; Tsutomu Kido, both of Ehime-ken; Yoshitaka Mishima, Kagawa-ken, all of Japan

[73] Assignee: Uni-Charm Corporation, Ehime-ken, Japan

[21] Appl. No.: 686,624

[22] Filed: Jul. 24, 1996

[30] Foreign Application Priority Data

Jul. 28, 1995 [JP] Japan .................................. 7-193580

[51] Int. Cl.⁶ ......................................................... A61F 13/16
[52] U.S. Cl. ........................... 604/390; 604/389; 604/391
[58] Field of Search .................................. 604/389, 391, 604/390, 358, 385.1

[56] References Cited

U.S. PATENT DOCUMENTS

| | | | |
|---|---|---|---|
| 4,402,690 | 9/1983 | Redfern | 604/391 |
| 4,568,344 | 2/1986 | Suzuki et al. | |
| 4,773,906 | 9/1988 | Krushel | 604/391 |
| 4,834,742 | 5/1989 | Wilson et al. | 604/391 |
| 4,923,456 | 5/1990 | Proxmire | 604/391 |
| 5,019,065 | 5/1991 | Scripps | 604/391 |
| 5,112,326 | 5/1992 | Quadrini | 604/391 |
| 5,269,776 | 12/1993 | Lancaster et al. | 604/391 |
| 5,401,275 | 3/1995 | Flug et al. | 604/389 |

FOREIGN PATENT DOCUMENTS

| | | |
|---|---|---|
| 0 113 464 | 12/1983 | European Pat. Off. |
| 0 563 458 | 4/1992 | European Pat. Off. |
| 6-61227 | 8/1994 | Japan |
| 2 284 742 | 6/1995 | United Kingdom |

*Primary Examiner*—John G. Weiss
*Assistant Examiner*—David J. Cho
*Attorney, Agent, or Firm*—Lowe Hauptman Gopstein Gilman & Berner

[57] ABSTRACT

A disposable undergarment having a tape fastener for releasably joining front and rear regions of the undergarment to each other is disclosed. The tape fastener includes a relatively soft base panel member extending laterally outward from a transverse side edge of the undergarment, relatively rigid fastening panel members provided at longitudinally spaced apart locations of the base panel member and an adhesive region provided between the fastening panel members.

9 Claims, 3 Drawing Sheets ns.patent.number: 5,851,205

DISPOSABLE UNDERGARMENT HAVING A TAPE FASTENER

BACKGROUND OF THE INVENTION

The present invention relates to a disposable undergarment having a tape fastener and, more specifically to an undergarment such as a disposable diaper for babies, a disposable incontinence diaper for adults, disposable training pants for babies and the like having an improved tape fastener.

Japanese Laid-Open Utility Model Application No. Hei6-61227 discloses a disposable diaper having a pair of tape fasteners laterally extending outward from transversely opposite edges of a rear body of the diaper. The tape fastener may be engaged with the other tape fastener bonded to an outer surface of a front region of the diaper for releasably joining the front and rear regions to each other along their transversely opposite edges. Examples of such tape fasteners are known under the trade marks of VELCRO or MAGIC TAPE.

At least one of the hook and loop components forming the tape fastener is sometimes selected to have a relative rigidity so as to be easily engaged with and/or disengaged from the other component. For disposable diapers, the component having a relatively high rigidity is often bonded to tape fasteners extending laterally outward from transversely opposite edges of one of the front and rear regions of the diaper so that this component having a relatively high rigidity may be engaged with and/or disengaged from the other relatively soft component provided on an outer surface of the other region. When the one component of the tape fastener is selected to have a relatively high rigidity, an engaging or disengaging operation will be facilitated but a disengaging force exerted on one end of this component may propagate through the entire component at once and the tape fastener may be unintentionally disengaged. As a result, body fluids may leak sideways if this occurs during use of the diaper.

Accordingly, it is a principal object of the invention to eliminate the problem that the whole of the tape fastener might otherwise be unintentionally disengaged at once.

SUMMARY OF THE INVENTION

According to the invention, there is provided a disposable diaper having a tape fastener extending laterally outward from a transverse side edge of one of front and rear regions for releasably joining these front and rear regions to each other. The tape fastener comprises a relatively soft base panel member extending laterally outward from the transverse side edge and has a base end and a free end. At least two relatively rigid fastening panel members are bonded to an inner surface of the base panel member. The fastening panel members are provided at longitudinally spaced apart locations of the base panel member to be engaged with a fastening region provided on an outer surface of the other of the front and rear bodies.

DETAILED DESCRIPTION OF THE PREFERRED EMBODIMENT

Figure 1:
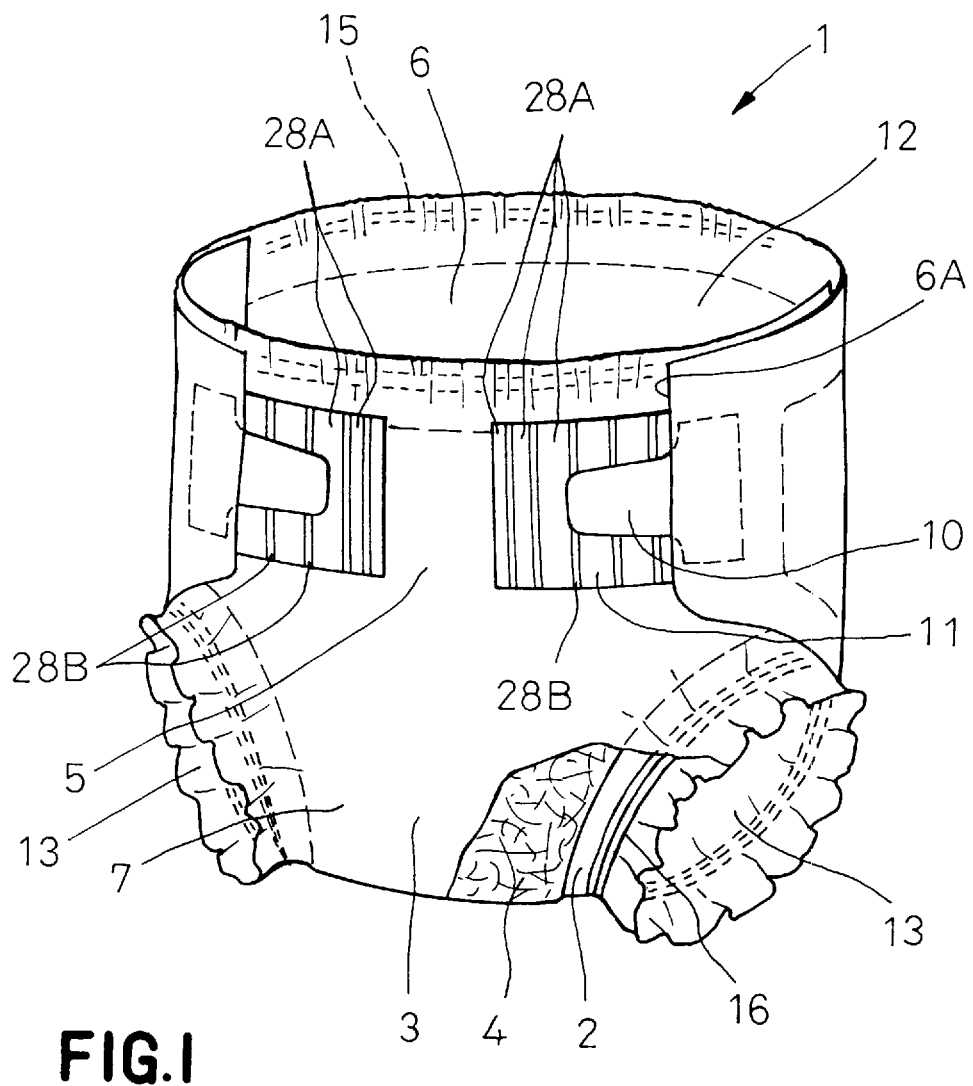
FIG. 1 is a perspective view, partially broken away, of a disposable diaper as an example of an undergarment of the invention.

FIG. 1 is a partially broken away perspective view of a diaper 1 as put on a user's body. The disposable diaper 1 comprises a liquid-permeable topsheet 2, a liquid-impermeable backsheet 3 and a liquid-absorbent core 4 disposed between these two sheets 2, 3. The diaper 1 is composed of a front region 5, a rear region 6 and a crotch region 7 longitudinally extending between these two regions 5, 6. Tape fasteners 10 extend laterally outward from transversely opposite side edges 6A of the rear region 6, respectively, and respective inner surfaces of these tape fasteners 10 are engaged with fastening regions 11 provided on an outer surface of the front region 5 at its transversely opposite edges. The diaper 1 is formed with a waist-opening 12 and a pair of leg-openings 13 as the front and rear regions 5, 6 are joined to each other in such a manner described above. The respective openings 12, 13 are circumferentially provided with elastically stretchable members 15, 16, respectively, which are bonded to at least one of respective inner surfaces of the top- and backsheets 2, 3.

Figure 2:
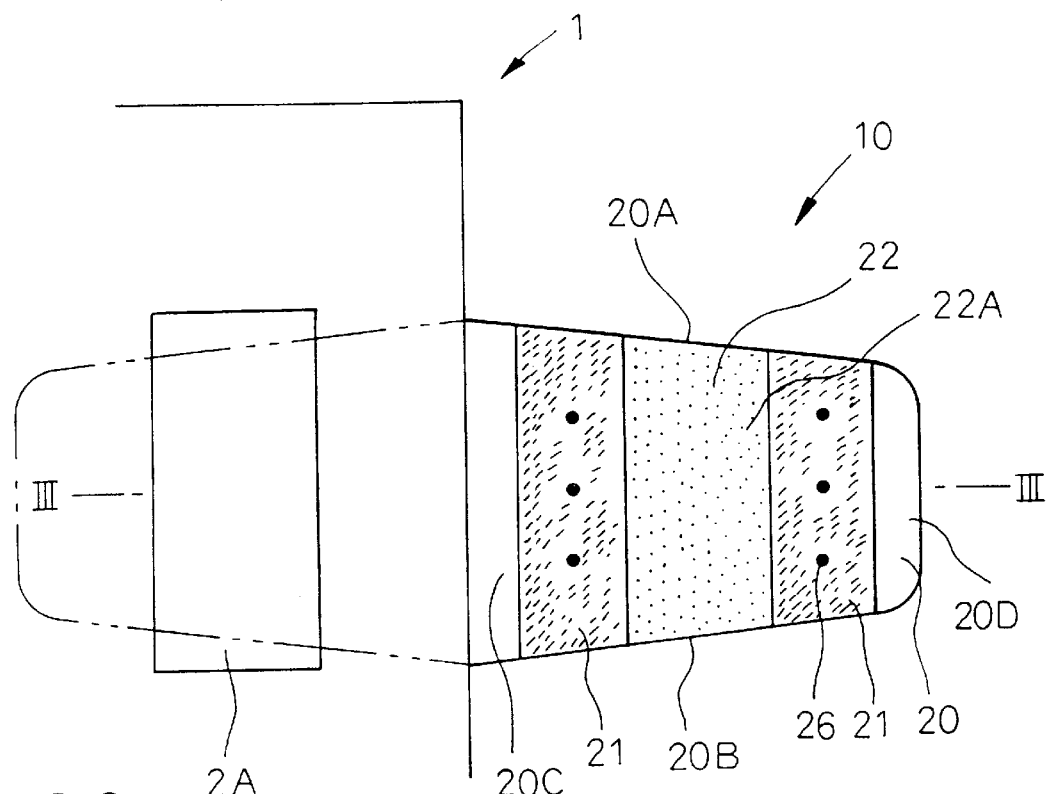
FIG. 2 is a plan view of a tape fastener.

The tape fastener 10 of which the inner side is shown by FIG. 2 comprises a soft base panel member 20 formed by a nonwoven fabric made of thermoplastic synthetic fibers and fastening panel members 21 made of plastic material having a rigidity higher than that of said sheet member 20. The fastening panel members 21 extend between upper and lower edges 20A, 20B of the base panel member 20 at locations spaced apart from each other, i.e., at a location adjacent a base end 20C and at a location adjacent a free end 20D with respect to the associated edge of the rear region 6 from which this tape fastener 10 laterally extends outward, and are fixedly bonded to the base panel member 20 by a means of an adhesive agent 22A and heat-sealing spots 26. The base panel member 20 is provided between the two fastening panel members 21 with an adhesive region 22 carrying the adhesive agent 22A exposed thereon. The free end 20D of the base panel member 20 is non-adhesive and serves as a pick-up means. The tape fastener 10 is shown in its position before use by an imaginary line in FIG. 2. Specifically, the tape fastener 10 is folded back onto the associated side edge inner surface of the diaper 1 with the adhesive region 22 being provisionally fixed to a releasing strip 2A on the diaper 1.

Figure 3:
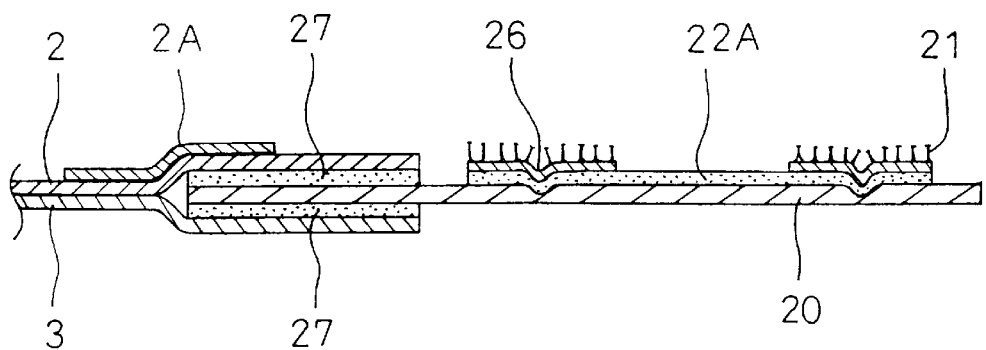
FIG. 3 is a sectional view taken along a line III—III in FIG. 2.

FIG. 3 is a sectional view taken along a line III—III in FIG. 2. As shown, a part of the base panel member 20 is bonded to respective inner surfaces of the top and backsheets 2, 3 by a means of hot melt adhesive 27. The spaced apart fastening panel members 21 are bonded to an upper surface of the adhesive agent 22 and heat-sealed to the base panel member 20 by means of the heat-sealing spots 26. It should be understood that the adhesive region 22 lies at a level lower than that of the fastening panel members 21. Each fastening panel member 21 comprises a plurality of hook elements of the tape fastener which are sold under the trade marks of VELCRO or MAGIC TAPE and made of nylon or any other suitable plastics. Each fastening region 11 with which the respective fastening panel members 21 are engaged comprises a bulky nonwoven fabric made of crimped fibers and corresponds to a plurality of loop elements of the known tape fastener. The fastening region 11 presents a plurality of vertically extending stripes as seen in FIG. 1 so that each of these stripes may be used as a positioning indicator when the fastening panel members 21 are engaged with the fastening region 11. This striped pattern is obtained by bonding a nonwoven fabric as material for the fastening region 11 to the backsheet 3 with use of colored hot melt adhesive, wherein the nonwoven fabric is applied with the colored hot melt adhesive in the desired striped pattern. Referring to FIG. 1, sections 28A are destined to be bonded to the backsheet 3 and present the color of the hot melt adhesive therethrough while sections 28B are not bonded to the backsheet 3 and present the color of the nonwoven fabric itself. The pattern in which the nonwoven fabric is applied with the hot melt adhesive and which serves as the positioning indicator may be selected from a group of appropriate patterns other than the striped pattern as adopted by the illustrated embodiment, so far as the adhesive is applied to the nonwoven fabric intermittently along the waist line.

Figure 4:
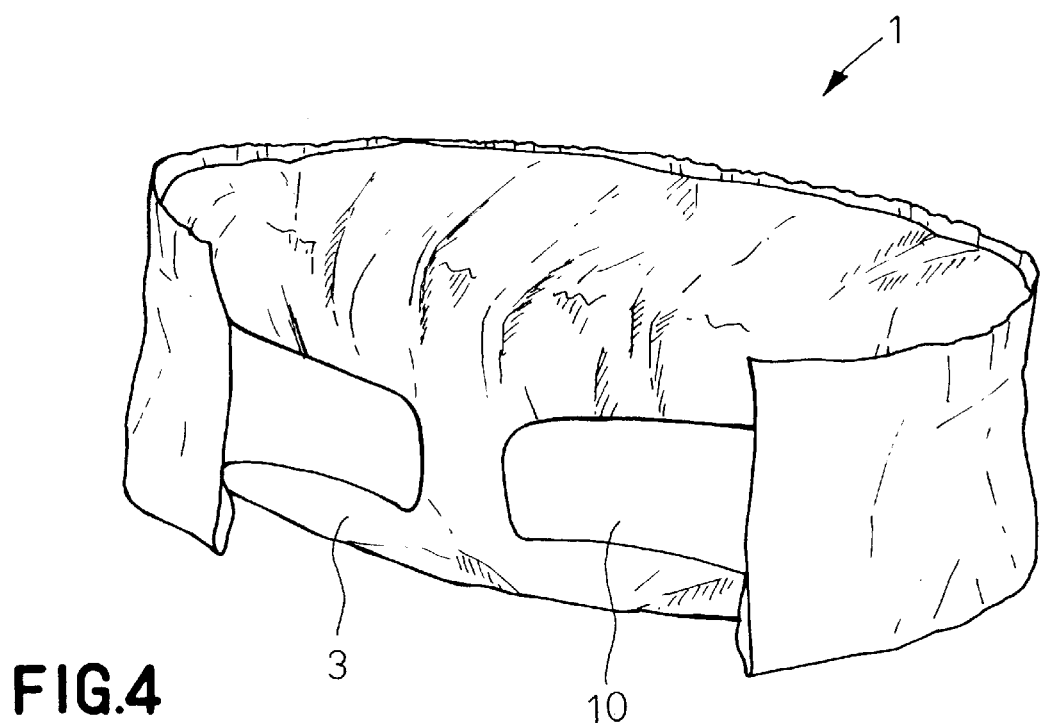
FIG. 4 is a perspective view of the diaper as rolled up.

FIG. 4 shows the diaper 1 as rolled up after use and maintained in such a rolled up state with the adhesive region 22 being fastened to the diaper 1 at an appropriate location thereof.

Figure 5:
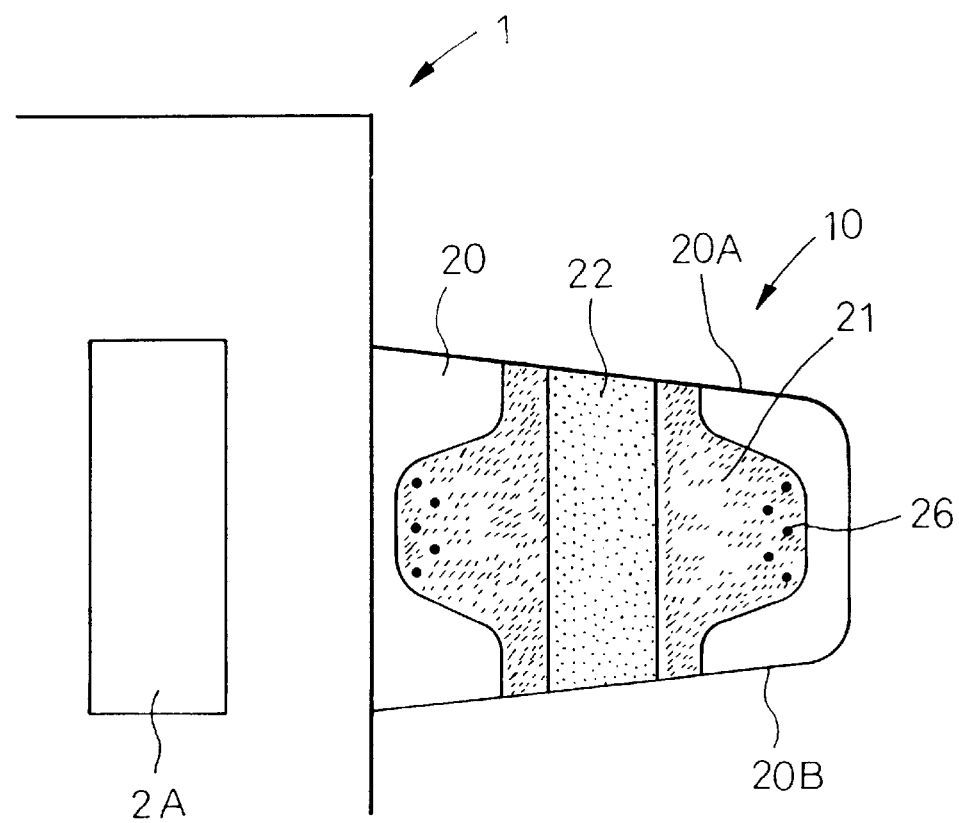
FIG. 5 is a view similar to FIG. 2 but of a tape fastener different from that depicted by FIG. 2.

FIG. 5 shows a tape fastener 10 including a fastening panel member 21 which has a configuration different from that shown by FIG. 2 as viewed in the plan view. According to this embodiment, the respective fastening panel members 21 extending between the upper and lower edges 20A, 20B of the base panel member 20 are transversely dimensioned so as to be relatively narrow in the proximity of the upper and lower edges 20A, 20B and relatively large at their vertically middle portions. Generally, the fastening panel member 21 is rather rigid and tends to irritate the user's skin particularly at the region in the proximity of the upper and lower edges 20A, 20B. However, the tape fastener 10 according to this embodiment can alleviate such undesirable irritation, since the fastening panel member 21 is transversely dimensioned to be relatively narrow in the proximity of the upper and lower edges 20A, 20B as previously described. In this case, the fastening effect of the tape fastener 10 is concentrated in its vertically middle portion which is substantially larger than its vertically opposite end portions in the proximity of the upper and lower edges 20A, 20B.

To implement the invention, a nonwoven fabric or soft plastic film may be employed as the base panel member 20 of the tape fastener 10 and the known hook or loop material may be employed as the fastening panel member 21. The invention can be effectively implemented even when the tape fastener 10 is not provided with the adhesive region 22. It is also possible without departing from the scope of the invention to bond the fastening panel member 21 to the base panel member 20 by use of a means having an adhesion force higher than an adhesion force of the adhesive agent 22A, for example, hot melt adhesive. The fastening region 11 may be of any suitable material other than a nonwoven fabric so far as the fastening panel member 21 can be disengaged therefrom.

It should be understood that not only the adhesive agent such as hot melt adhesive but also the heat-sealing technique may be employed for bonding of the respective members, the latter being useful for the members made of a heat-sealable material.

According to the invention, the soft base panel member 20 extending laterally outward from the transverse side edge of the diaper is provided with a pair of fastening panel members 21 spaced apart from each other, i.e., at a location adjacent the base end 20C and at a location adjacent the free end 20D thereof, so that, even if one of the spaced apart fastening panel members 21, for example, the one provided in the proximity of the free end 20D of the base panel member 20 is unintentionally disengaged from the fastening region 11, the other one provided in the proximity of the base end 20C of the base panel member 20 will not be affected by the disengaging force exerted on the fastening panel member 21 provided in the proximity of the free end 20D of the base panel member 20. The invention thereby can avoid an apprehension that unintentional release of one fastening panel member 21 might lead at once to release of the tape fastener 10 as a whole.

With an embodiment in which the base panel member 20 is provided with an adhesive region 22 between the pair of fastening panel members 21, this adhesive region 22 may serve as an effective means by which a used diaper can be rolled up. Advantageously, formation of such an adhesive region 22 requires no enlargement of the base panel member's dimensions, in particular its length.

What is claimed is:

1. In a disposable undergarment having a front waist region and a rear waist region and at least one tape fastener connected to secure the regions together during use, the improvement comprising:

said tape fastener including a relatively soft base panel member extending laterally outward from a transverse side edge of said rear waist region and having a base end and a free end, inner and outer surfaces and upper and lower edges, and at least two relatively rigid fastening panel members having a plurality of one hook elements and loop elements provided at longitudinally spaced apart locations on the inner surface between the upper and lower edges of said base panel member, and an adhesive region provided on the inner surface of said base panel member between said fastening panel members;

said fastening panel members being fixedly bonded to the inner surface of said base panel member; and a fastening region having a plurality of the other of said hook elements and loop elements provided on an outer surface of said front waist region to be releasably engaged with said fastening panel members, wherein said fastening panel members are arranged such that, even if one of the spaced apart fastening panel members is inadvertently disengaged from said fastening region with a disengaging force, the other one of said fastening panel members is unaffected by the disengaging force to thereby remain in fastening contact with said fastening region, and wherein said adhesive region is provided between said fastening panel members to enable a soiled said disposable undergarment to be rolled up and remain in a rolled condition with said adhesive regions.

2. The undergarment according to claim 1, wherein said fastening panel members respectively are at least at a location adjacent the base end and a location adjacent the free end of said base panel member.

3. The undergarment according to claim 1, wherein said base panel member is made of nonwoven fabric of thermoplastic synthetic fibers, and said fastening panel members are made of a plastic material having a rigidity higher than that of said base panel member.

4. In the disposable undergarment of claim 1, wherein said fastening panel members are fixedly bonded to the inner surface of said base panel member with heat sealing spots.

5. In the disposable undergarment of claim 1, wherein said fastening panel members are fixedly bonded to the inner surface of said base panel member with a hot melt adhesive and heat sealed partially to the inner surface of said base panel member.

6. In a disposable undergarment having a front waist region and a rear waist region and at least one tape fastener connected to secure the regions together during use, the improvement comprising:

said tape fastener including a relatively soft base panel member extending laterally outward from a transverse side edge of said rear waist region and having a base end and a free end, inner and outer surfaces and upper and lower edges, and at least two relatively rigid fastening panel members having a plurality of hook elements provided at longitudinally spaced apart locations on the inner surface between the upper and lower edges of said base panel member and which are transversely dimensioned so as to be relatively narrow in the proximity of the upper and lower ends of said base panel member and relatively large at a vertical midportion thereof between the upper and lower ends of said base panel member, said fastening panel members being fixedly bonded to the inner surfaces of the base panel member by a hot melt adhesive and heat-sealed partially to the inner surface of the base panel member, and an adhesive region provided on the inner surface of said base panel member between said fastening panel members; and a fastening region having a plurality of loop elements provided on an outer surface of said front waist region to be releasably engaged with said fastening panel members.

7. The undergarment according to claim 6, wherein said fastening panel member respectively are at least at a location adjacent the base end and a location adjacent the free end of said base panel member.

8. The undergarment according to claim 6, wherein said base panel member is made of nonwoven fabric of thermoplastic synthetic fibers, and said fastening panel members are made of a plastic material having a rigidity higher than that of said base panel member.

9. The undergarment according to claim 6, wherein said fastening panel members are fixedly bonded to the inner surfaces of said base panel member with hot melt adhesive and heat-sealed partially to the inner surface of said base panel member with heat-sealing spots.

* * * * *